(12) United States Patent
Hamilton et al.

(10) Patent No.: US 7,288,648 B2
(45) Date of Patent: Oct. 30, 2007

(54) HIGH TEMPERATURE CRYSTALLIZATION OF 2,4,6,8,10,12-HEXANITRO-2,4,6,8,10,12-HEXAAZATETRACYCLO[5.5.0.05,903,11]-DODECANE

(75) Inventors: R. Scott Hamilton, Bear River City, UT (US); Vincent Mancini, Ogden, UT (US); Clint Nelson, Perry, UT (US); Sharon Yeung Dressen, Ogden, UT (US)

(73) Assignee: Alliant Techsystems Inc., Edina, MN (US)

( * ) Notice: Subject to any disclaimer, the term of this patent is extended or adjusted under 35 U.S.C. 154(b) by 446 days.

(21) Appl. No.: 10/636,373

(22) Filed: Aug. 6, 2003

(65) Prior Publication Data

US 2007/0225493 A1    Sep. 27, 2007

Related U.S. Application Data

(63) Continuation-in-part of application No. 09/972,360, filed on Oct. 5, 2001, now abandoned.

(60) Provisional application No. 60/238,008, filed on Oct. 6, 2000.

(51) Int. Cl.
*C07D 487/22* (2006.01)
*C07B 25/34* (2006.01)
*C07B 45/00* (2006.01)

(52) U.S. Cl. .................... 540/554; 149/92

(58) Field of Classification Search ........... 540/554; 149/92

See application file for complete search history.

(56) References Cited

U.S. PATENT DOCUMENTS

| | | | |
|---|---|---|---|
| 5,099,008 A | 3/1992 | Voigt, Jr. et al. | 540/475 |
| 5,587,553 A | 12/1996 | Braithwaite et al. | 149/19.6 |
| 5,693,794 A | 12/1997 | Nielsen | 540/554 |
| 5,712,511 A | 1/1998 | Chan et al. | 264/3.4 |
| 5,723,604 A | 3/1998 | Cannizzo et al. | 540/556 |
| 5,739,325 A | 4/1998 | Wardle et al. | 540/554 |
| 5,750,921 A | 5/1998 | Chan et al. | 149/19.92 |
| 5,874,574 A | 2/1999 | Johnston et al. | 540/475 |
| 5,936,196 A | 8/1999 | Dawson | 149/92 |
| 5,942,722 A | 8/1999 | Dawson | 149/92 |
| 5,973,149 A | 10/1999 | Bescond et al. | 544/345 |
| 6,160,113 A | 12/2000 | Duddu et al. | 540/554 |
| 6,217,799 B1 | 4/2001 | Lee et al. | 264/3.3 |
| 6,350,871 B1 | 2/2002 | Sanderson et al. | 540/554 |

FOREIGN PATENT DOCUMENTS

| | | |
|---|---|---|
| EP | 0 753 519 B1 | 5/2000 |
| EP | 1 327 633 A1 | 7/2003 |
| JP | 2000128685 A2 | 5/2000 |
| WO | WO98/27072 A1 | 6/1998 |

OTHER PUBLICATIONS

Nielsen et al., "Polyazapolycyclics by Condensation of Aldehydes with Amines. 2. Formation of 2,4,6,8,10,12 Hexabenzyl 2,4,6,8,10,12 hexaazatetra cyclo [$5.5.0.0^{5.9}.0^{3,11}$] dodecanes from Glyoxal and Benzylamines," Journal of Organic Chemistry, vol. 55, pp. 1459-1466 (1990).

French Search Report, dated Aug. 29, 2005.

Bolotina, Nadezhda B., et al., "Energetic materials: variable-temperature crystal structures of y- and e- HNIW polymorphs," J. Appl. Cryst., vol. 37, pp. 808-814, 2004.

Nedelko, V.V., et al., "Comparative Investigation of Thermal Decomposition of Various Modifications of Hexanitrohexaazaisowurtzitane," 31st International Annual Conference of ICT (Energetic Materials), pp. 9/1-9/9, 2000, ISSN: XP009052414.

Von Holtz, Erica, et al., "The Solubility of e-CL-20 in Selected Materials," Propellants, Explosives, Pyrotechnics, vol. 19, pp. 206-212, 1994.

*Primary Examiner*—Brenda Coleman
(74) *Attorney, Agent, or Firm*—TraskBritt

(57) ABSTRACT

A method of crystallizing an epsilon-polymorph of 2,4,6,8,10,12-hexanitro-2,4,6,8,10,12-hexaazatetracyclo[$5.5.0.0^{5,9}$ $0^{3,11}$]-dodecane (CL-20). The method comprises combining the CL-20, at least one organic solvent, and at least one nonsolvent to form a crystallization solution. The crystallization solution is saturated and heated to a temperature greater than about 60° C., such as from about 71° C. to about 94° C. The organic solvent is removed from the crystallization solution while retaining a sufficient amount of the nonsolvent to crystallize the CL-20 as the epsilon-polymorph. The nonsolvent is separated from the epsilon-polymorph of CL-20. A composition of CL-20 comprising the epsilon-polymorph having a particle density of 2.035 g/ml is also disclosed.

19 Claims, No Drawings

US 7,288,648 B2

HIGH TEMPERATURE CRYSTALLIZATION OF 2,4,6,8,10,12-HEXANITRO-2,4,6,8,10,12-HEXAAZATETRACYCLO[5.5.0.05,903,11]-DODECANE

CROSS-REFERENCE TO RELATED APPLICATION

This application is a continuation-in-part of U.S. patent application Ser. No. 09/972,360, filed on Oct. 5, 2001 now abandoned, which claims the benefit of priority of U.S. Provisional Application 60/238,008, filed on Oct. 6, 2000, the complete disclosure of which is incorporated herein by reference.

GOVERNMENT LICENSE RIGHTS

The U.S. Government has a paid-up license in this invention and the right in limited circumstances to require the patent owner to license others on reasonable terms as provided for by the terms of contract N00174-99-C-0030 awarded by the Indian Head Division of the Naval Surface Warfare Center.

BACKGROUND OF THE INVENTION

1. Field of the Invention

The present invention relates to an improved method of crystallizing 2,4,6,8,10,12-hexanitro-2,4,6,8,10,12-hexaazatetracyclo[$5.5.0.0^{5,9}0^{3,11}$]-dodecane, hereinafter referred to as CL-20. More specifically, the present invention relates to a high temperature method of crystallizing an epsilon-polymorph of CL-20.

2. State of the Art

For many existing propellant and weapons systems, a critical ingredient in terms of propulsive and explosive performance is an oxidizer or energetic filler, such as CL-20. CL-20, with its substantial increase in performance output, is an organic oxidizer/filler presenting significant opportunities in terms of energy capabilities for propellants and explosives. For example, using CL-20 as the energetic filler or propellant component in weapons systems may provide increased anti-armor penetration, enhanced missile payload velocity and flight, increased underwater torpedo effectiveness and lethality, and improved gun propellant impetus.

The performance of CL-20 in propellant and weapons systems is highly dependent upon the crystal polymorph of CL-20. CL-20 has several different crystal polymorphs including the alpha-polymorph ("α-polymorph"), the beta-polymorph, the epsilon-polymorph ("ε-polymorph"), and the gamma-polymorph. The ε-polymorph is known in the art and has high energetic performance, high density, and low sensitivity compared to the other polymorphs, which makes the ε-polymorph more desirable for use in propellant and weapons systems. However, many conventional CL-20 synthesis techniques produce the α-polymorph as the predominant crystal polymorph, which has a much lower density than the ε-polymorph. Therefore, the CL-20 synthesized by many conventional techniques must be dissolved and recrystallized to increase the proportion of the ε-polymorph.

Conventionally, CL-20 has been crystallized using a chloroform nonsolvent to precipitate the CL-20 from ethyl acetate. Chloroform has been found to produce the desirable ε-polymorph of CL-20 consistently and reproducibly. However, one disadvantage of using chloroform as the nonsolvent is that defects, such as voids and multiple crystalline shapes (agglomerates), are often found in the crystalline structure of the ε-polymorph CL-20. Another disadvantage of this conventional technique is that the chloroform and the ethyl acetate cannot be effectively and efficiently separated by distillation, which complicates their reuse. Because the chloroform cannot be easily reused, a continual discharge of a chlorinated waste stream must be disposed of in an environmentally acceptable manner. As a chlorinated compound that potentially contributes to ozone depletion, the waste disposal of chloroform and other chlorinates is complicated. Therefore, it is advantageous to crystallize CL-20 into the ε-polymorph with solvents and nonsolvents that can be recycled within the crystallization process without producing a discharge of chlorinated or halogenated waste.

A CL-20 crystallization technique that avoids the use of chloroform and other chlorinated solvents and nonsolvents is disclosed in U.S. Pat. No. 5,874,574 to Johnston et al., which describes dissolving CL-20 in a solution containing a CL-20 solvent, such as ethyl acetate. A low density CL-20 nonsolvent is then added to the dry CL-20 solvent phase to crystallize the ε-polymorph of CL-20. Nonsolvents include aromatics, such as benzene and toluene and the like, and relatively lower carbon number hydrocarbons. A drawback to this process, however, is that multiple shapes of CL-20 crystals are formed. The lack of uniformity in crystalline shape raises the viscosity of compositions that CL-20 is blended into, which adversely affects the capability to attain high solid loadings. Also, the lack of uniformity between separate production lots of CL-20 lowers predictability of explosives and propellants containing the CL-20.

Another CL-20 crystallization technique is disclosed in U.S. Pat. No. 5,973,149 to Bescond et al., in which ε-polymorph CL-20 is crystallized from a saturated solution of an organic solvent and a nonsolvent. The organic solvent is an ester, nitrite, ether, or ketone (with the exception of acetone). The nonsolvent is an aliphatic hydrocarbon, aromatic hydrocarbon, or mixtures thereof. The saturated solution is seeded with crystals of ε-polymorph CL-20 and then is concentrated by evaporation to produce CL-20 particles having particle size fractions within the 10 micron to 100 micron range. The small particle sizes of these crystals can be disadvantageous where relatively slow burn rates are desired or either bimodal or trimodal formulations are needed to tailor processability and/or ballistic properties.

To overcome these problems, it would be desirable to provide a method of producing the ε-polymorph of CL-20 that possesses a reproducible crystal shape and excellent quality in high yields. The method should be environmentally friendly and more economically efficient than known methods.

SUMMARY OF THE INVENTION

The present invention relates to a method of crystallizing an ε-polymorph of CL-20. The method comprises combining the CL-20, at least one organic solvent, and at least one nonsolvent to form a crystallization solution. The organic solvent may be ethyl acetate and the nonsolvent may be a formate or an acetate, such as benzyl acetate or benzyl formate. A co-nonsolvent may optionally be used in the crystallization solution. The co-nonsolvent may be a naphthenic oil and/or a paraffinic oil. The crystallization solution is saturated and heated to a temperature greater than about 60° C., such as from about 71° C. to about 94° C. Optionally, ε-polymorph CL-20 seed crystals may be added to the saturated crystallization solution. The organic solvent is removed from the crystallization solution while retaining a sufficient amount of the at least one nonsolvent to crystallize the CL-20 as the ε-polymorph. The organic solvent may be evaporated from the crystallization solution under vacuum or by blowing a dry gas over the crystallization solution, leaving behind a slurry of the ε-polymorph of the CL-20 in the nonsolvent.

The present invention also relates to a composition of CL-20 comprising an ε-polymorph of CL-20 having an average particle density ranging from approximately 2.034 g/ml to approximately 2.036 g/ml. The ε-polymorph of CL-20 may be used in an explosive composition comprising additional components, such as a binder, a plasticizer, a fuel, an inorganic oxidizer, a curative, or combinations thereof.

DETAILED DESCRIPTION OF THE INVENTION

An ε-polymorph of CL-20 is produced by crystallizing CL-20 crystals from a solution including at least one organic solvent and at least one nonsolvent. The ε-polymorph of CL-20 may be crystallized from a crystallization solution including the organic solvent, the nonsolvent, and the CL-20 at a temperature above 60° C. The CL-20 used in the crystallization solution may include a mixture of CL-20 polymorphs, such as a mixture of the α-polymorph, the beta-polymorph, the ε-polymorph, and/or the gamma-polymorph.

The crystallization method of the present invention may be used to crystallize CL-20 that has been synthesized by a conventional synthetic route. Various methods of synthesizing CL-20, from various precursors, are known in the art. As such, the synthesis of the CL-20 is not described in detail herein. The present method may be especially useful for crystallizing CL-20 synthesized by nitrating 2,6,8,12-tetraacetyl-2,4,6,8,10,12-hexaazatetracyclo-[$5.5.0.0^{5,9}0^{3,11}$]-dodecane ("TADH" or "TADA"). The nitration of TADH is known in the art, such as described in EP 0 753 519. The nitration may be carried out in a mixed acid comprising nitric acid ("$HNO_3$") and a strong acid, such as sulfuric acid ("$H_2SO_4$"). Although sulfuric acid may be used in combination with the nitric acid, it is also contemplated that nitric acid may be used alone. According to one example of a method of nitrating TADH, the nitration may be performed at 85° C., with the weight ratio of nitric acid to sulfuric acid ($HNO_3:H_2SO_4$) in a range of from about 6:4 to about 8:2, such as about 7:3. The ratio of mixed acid (in milliliters) to TADH (in grams) may be in a range of from about 3:1 to about 30:1, such as from about 4:1 to about 8:1, or such as about 6:1. The acid mixture may include up to about 8% by weight of water. However, it is also contemplated that the acid mixture may be substantially free of water. For instance, the acid mixture may have less than about 2.5% by weight of water, such as less than 1% by weight of water. Prior to crystallization, a CL-20 feed may be pretreated to neutralize any residual acids, such as nitric and sulfuric acids. For instance, the CL-20 feed may be treated with a neutralizing agent, such as sodium bicarbonate.

TADH is available from Asahi of Osaka, Japan. TADH may also be prepared from hexabenzylhexaazaisowurtzitane ("HBIW") as a precursor. Preparation of TADH from HBIW is described, for example, in EP 0 753 519. HBIW may be synthesized according to the procedure described by Nielsen et al. in "Polyazapolycyclics by Condensation of Aldehydes with Amines. 2. Formation of 2,4,6,8,10,12-Hexabenzyl-2,4,6,8,10,12-hexaazatetra-cyclo-[$5.5.0.0^{5,9}0^{3,11}$]-dodecanes from Glyoxal and Benzylamines," Journal of Organic Chemistry, Vol. 55, pp. 1459-66 (1990) and U.S. Pat. No. 5,723,604, the complete disclosures of which are incorporated herein by reference.

While one method of synthesizing CL-20 has been described above, it is understood that the crystallization method of the present invention may be performed on CL-20 prepared from other precursors, such as TADF ("tetraacetyldiformylhexaazaisowurtzitane").

The at least one organic solvent and the at least one nonsolvent used in the crystallization solution may be miscible with each other. While is it desirable for the organic solvent and the nonsolvent to be miscible, it is also contemplated that the organic solvent and the nonsolvent may be partially miscible or immiscible with each other. As used herein, the term "organic solvent" refers to an organic solvent in which at least 10% weight/weight (g/g) of CL-20 is soluble. Desirably, at least 20% weight/weight (g/g) of CL-20 is soluble in the organic solvent. In other words, the organic solvent has a relatively high solubility of CL-20. It is also contemplated that an organic solvent having a lower solubility of CL-20 may be used; however this may be less economically feasible than using an organic solvent with a higher solubility of CL-20. The organic solvent may also have a relatively low boiling point compared to the boiling point of the nonsolvent. The low boiling point of the organic solvent may allow the organic solvent to evaporate while leaving sufficient nonsolvent in the crystallization solution to collect the CL-20 crystals. The organic solvent may be a nonhalogenated solvent and may include, but is not limited to, lower alkyl acetates such as methyl acetate, ethyl acetate, propyl acetate, and isopropyl acetate; ketones such as acetone and methyl ethyl ketone; cyclic ethers such as tetrahydrofuran; nitromethane; and acetonitrile. In one embodiment, ethyl acetate is used as the organic solvent because of its low boiling point and environmental acceptability compared to chlorinated solvents. The organic solvent may also be a halogenated solvent, such a halogenated acetate or a halogenated ketone. An effective amount of the organic solvent may be used in the crystallization solution to completely dissolve the CL-20 prior to commencement of crystallization.

To permit the organic solvent to be separated from the CL-20 by evaporation or the like while retaining a sufficient amount of the nonsolvent for receiving the CL-20 crystals, the nonsolvent used in the crystallization solution may have a low volatility and a boiling point that is at least about 10° C. higher than the boiling point of the organic solvent. For instance, the boiling point of the nonsolvent may be at least 15° C. higher or at least 20° C. higher than the boiling point of the organic solvent(s). The nonsolvent used in the crystallization solution may include at least one formate or at least one acetate, such as an organic ester, that has a relatively low vapor pressure at ambient pressure compared to the vapor pressure of the organic solvent. The nonsolvent may be an aryl formate or an aryl acetate. Examples of aryl formates include, but are not limited to, phenyl formate; phenalkyl formates, such as benzyl formate and phenethyl formate; and benzoyl formates, such as 1-methylpropyl benzoyl formate. The aryl formate may also include substitutents, such as in the case of 4-methoxy benzyl formate, multiple formate moieties, and/or heteroatoms. Nonaromatic formates, such as alkyl formate (e.g., heptyl formate), ethylene glycol diformate, triethylene glycol diformate, and diethylene glycol diformate, may also be used as the nonsolvent as long as the organic solvent used in the crystallization solution has a sufficiently low boiling point. Examples of aryl acetates include, but are not limited to, phenyl acetate; phenalkyl acetates, such as benzyl acetate and phenethyl acetate; and benzoyl acetates, such as 1-methylpropyl benzoyl acetate. The aryl acetate may also include substitutents, such as in the case of 4-methoxy benzyl acetate, multiple acetate moieties, and/or heteroatoms. Nonaromatic acetates, such as alkyl acetates (e.g., heptyl acetate), ethylene glycol diacetate, triethylene glycol diacetate, and diethylene glycol diacetate, may also be used as the nonsolvent as long as the organic solvent has a sufficiently low boiling point. In one embodiment, the nonsolvent is benzyl acetate or benzyl formate.

By selecting the organic solvent and the nonsolvent to meet these criteria, the nonsolvent may be retained during evaporation of the organic solvent, even when the organic solvent is evaporated under vacuum or with the aid of a dry gas, such as nitrogen.

The nonsolvent may be present in the crystallization solution at a weight ratio of nonsolvent to CL-20 of not less than about 2:1. For instance, the nonsolvent may be present in a range of from about 5:1 to about 8:1. The presence of less than about 3:1 weight ratio of the nonsolvent to CL-20 may lead to the formation of defects in the CL-20 during crystallization. On the other hand, operating at a weight ratio of more than about 8:1 is economically inefficient because using these high ratios may require longer processing times, more manpower, and larger operating equipment. Also, it is desirable to completely dissolve the CL-20 into the organic solvent and the nonsolvent prior to saturating the solution and commencing crystallization. Excess nonsolvent may interfere with the ability to dissolve all of the CL-20 into the solution.

The nonsolvents, such as the formates and acetates, may be used alone or in combination with each other and, optionally, may be used in combination with co-nonsolvents. For instance, the nonsolvents may be used in combination with hydrocarbon mixtures, such as naphthenic and/or paraffinic oils, as the co-nonsolvents. Examples of the co-nonsolvents may include, but are not limited to, STANPLAS® 100, STANPLAS® 300, STANPLAS® 500, STANPLAS® 1200, SUNPAR® 120, and SUNPAR® 150, which are refined naphthenic oils or paraffinic oils. The STANPLAS® oils are distributed through Harwick Standard Distribution Corp. (Akron, Ohio). The SUNPAR® oils are available from Sun Oil Company N.V. (Belgium). Another useful co-nonsolvent is poly(propylene glycol) ("PPG"). The co-nonsolvents may also be hydrocarbons, such as hexane, heptane, octane, and higher chain lengths, as well as branched, cyclic, aromatic, and halogenated hydrocarbons. In addition, ethers having acceptable boiling points may be used as the co-nonsolvent. The co-nonsolvents may reduce the solubility of the crystallized CL-20 in the crystallization solution as the organic solvent is evaporated, which increases the yield of recovered CL-20 crystals. The amount of co-nonsolvent used in the crystallization solution may be determined by the concentration that will produce the highest yield while still maintaining an acceptable monocrystalline geometry. The co-nonsolvent may be present in a weight ratio of co-nonsolvent to nonsolvent of no more than about 90:10. For example, the co-nonsolvent may be present in a range of from about 20:80 to about 60:40, such as about 50:50. While the examples below describe using STANPLAS® 100 as the co-nonsolvent, it is understood that other co-nonsolvents may be used in the present invention. It is further understood that while the co-nonsolvent is optionally used in the crystallization solution, its use may result in a more cost-effective method of crystallizing the $\epsilon$-polymorph.

The order of combining the CL-20, the organic solvent, and the nonsolvent to form the crystallization solution is not critical to the operability of the present invention. Therefore, many sequences may be contemplated for combining these components to form the crystallization solution. For example, the CL-20 may be dissolved in the organic solvent and this mixture added to the nonsolvent. Alternatively, the CL-20, the organic solvent, and the nonsolvent may be combined. Once the crystallization solution is prepared, the crystallization solution may be saturated or supersaturated by various techniques. As used herein, saturated solutions encompass solutions at their saturation points or exceeding their saturation points (i.e., supersaturated). For instance, a sufficient volume of the nonsolvent may be added to the crystallization solution to reach or exceed the saturation point. Alternatively, the crystallization solution may be saturated by introducing additional CL-20 to the crystallization solution, evaporating a portion of the organic solvent from the crystallization solution, or a combination thereof. The organic solvent may be evaporated or removed from the crystallization solution under vacuum or in the presence of a blowing dry gas or the like, such as nitrogen.

The $\epsilon$-polymorph of CL-20 may be crystallized from the saturated or supersaturated solution by adding seed crystals of the $\epsilon$-polymorph to the crystallization solution and evaporating the organic solvent. The $\epsilon$-polymorph seed crystals may have a diameter ranging from approximately 30 µm to approximately 200 µm. However, $\epsilon$-polymorph seed crystals having smaller or larger diameters may also be used. To obtain $\epsilon$-polymorph seed crystals in this range, $\epsilon$-polymorph CL-20 crystals may be ground or milled by techniques known in the art, such as by a fluid energy mill or a ball mill. For instance, $\epsilon$-polymorph CL-20 crystals having a diameter from above 100 µm to about 200 µm may be ground to a diameter of not more than about 30 µm. The amount of CL-20 seed crystals added to the saturated solution may depend upon the desired crystal sizes of the crystals to be grown. CL-20 seed crystals may be added to the saturated solution in an amount ranging from approximately 0.001 g/100 g of dissolved CL-20 to approximately 10 g/100 g of dissolved CL-20. For instance, the CL-20 seed crystals may be added in an amount ranging from approximately 0.005 g/100 g of dissolved CL-20 to approximately 1.5 g/100 g of dissolved CL-20.

While the examples below describe using seed crystals, it is understood that the F-polymorph of CL-20 may also be crystallized from the crystallization solution without using seed crystals. For instance, the organic solvent may be completely removed or evaporated from the crystallization solution by heating the crystallization solution, such as at a temperature from greater than about 60° C. to about 130° C., as described in detail herein.

The organic solvent may be evaporated azeotropically from the crystallization solution to simultaneously remove any water present in the crystallization solution. The azeotropic evaporation of the organic solvent may be performed subsequent to introducing the CL-20 seed crystals into the crystallization solution. Alternatively, the azeotropic evaporation of the organic solvent may partially or completely overlap with the introduction of the seed crystals. For instance, the CL-20 seed crystals may be added to the crystallization solution before the occurrence of excessive supersaturation, which may be caused by evaporating large amounts of the organic solvent without simultaneous crystallization of the CL-20 from the crystallization solution.

High crystallization rates may be avoided by selecting an acceptable crystallization temperature. It was previously believed, as described in U.S. patent application Ser. No. 09/972,360, filed on Oct. 5, 2001, that an optimal crystallization temperature ranged from about 25° C. to about 60° C. At a crystallization temperature within this range, evaporation or removal of the organic solvent took approximately 16 hours, which resulted in excess product attrition and personnel labor charges. It was also observed that excess organic solvent remained in the crystallization solution, which resulted in a yield of about 60% of the F-polymorph of CL-20. It was further believed that operating at temperatures higher than 60° C. would lead to the formation of polymorphs other than the desired ε-polymorph.

It has recently been determined that a crystallization temperature of greater than 60° C. may be used to obtain the ε-polymorph. For instance, the ε-polymorph may be obtained at a crystallization temperature ranging from greater than about 60° C. to about 130° C., although this range may vary slightly depending upon the boiling points of the organic solvent and the nonsolvent. For instance, the crystallization may be performed at a temperature of from about 71° C. to about 94° C. By increasing the crystallization temperature, the rate of removal of the organic solvent from the crystallization solution may be increased, which decreases the amount of time required to remove the organic solvent. Without being bound to a particular theory, it is believed that the presence of the nonsolvent and the optional co-nonsolvent at this temperature range helps to reduce the conversion (or morphing) of one polymorph to another. In contrast, heating neat CL-20 crystals (CL-20 crystals without the organic solvent, nonsolvent, and/or co-nonsolvent) above 60° C. produces the gamma polymorph.

The temperature of greater than 60° C. may also more completely remove the organic solvent from the crystallization solution, which results in an increased yield of the F-polymorph relative to the yield obtained at temperatures lower than 60° C. For instance, yields of greater than approximately 60% may be achieved, such as yields ranging from approximately 75% to approximately 85%. Failure to remove a substantial portion of the organic solvent (e.g., about 90 wt % of the organic solvent) during crystallization of the CL-20 may lead to low recovery yields and defects in the crystallinity of the CL-20 occurring during recovery.

To produce commercial quantities of the ε-polymorph according to the present invention, a conventional reactor that is appropriate for crystallizing CL-20 may be used. For instance, a 500-lb reactor may be used, such as model no. QA1500 GUS available from Tycon Reactor (Venezia, Italy). The reactor may include a mixing device, such as a stir shaft, configured to mix the components of the crystallization solution. The reactor may also include a port configured to apply a vacuum or to direct a dry gas over the crystallization solution. Additionally, the reactor may include a temperature device configured to provide variable temperature settings. For instance, the temperature device may include a water jacket, wherein heat applied to the water in the water jacket is transferred to the reactor.

After removing the organic solvent and crystallizing the ε-polymorph of CL-20 in the nonsolvent, the crystalline CL-20 may be separated from the nonsolvent by solid-liquid separation techniques. Solid-liquid separation techniques are known in the art and, as such, are not discussed in detail herein. For example, the ε-polymorph CL-20 crystals may be filtered from the nonsolvent and then washed with an organic liquid. If a viscous nonsolvent is used, it may be necessary or desirable to lower the viscosity of the nonsolvent by diluting the crystallization solution in a recovery nonsolvent having a low viscosity. Examples of organic liquids for washing the ε-polymorph CL-20 crystals and, where appropriate, lowering the viscosity of the nonsolvent may include, but are not limited to, isopropanol, ethanol, and ethers, such as dialkyl ethers. For instance, diethyl ether may be used. Chlorinated solvents, such as methylene chloride, may also be used. However, the chlorinated solvents are less desirable because their use raises environmental problems.

The crystallization process may produce high-quality ε-polymorph CL-20 crystals having few crystal defects. The ε-polymorph CL-20 crystals may have a diameter ranging from approximately 1 µm to approximately 1 mm. Desirably, the ε-polymorph CL-20 crystals have a diameter from approximately 30 µm to approximately 300 µm. The ε-polymorph CL-20 crystals may also have a higher particle density than ε-polymorph CL-20 crystals crystallized by conventional techniques. In other words, a larger percentage of the ε-polymorph CL-20 crystals may have a higher particle density than ε-polymorph CL-20 crystals crystallized by conventional techniques. For instance, the ε-polymorph CL-20 crystals crystallized by the method of the present invention may have a distribution of particle densities ranging from approximately 2.018 g/ml to approximately 2.044 g/ml. An average particle density of the ε-polymorph CL-20 crystals crystallized by the method of the present invention may range from approximately 2.034 g/ml to approximately 2.036 g/ml. The ε-polymorph CL-20 crystals also exhibit enhanced reproducibility and lower shock sensitivity compared to CL-20 crystallized by known techniques. Additionally, the solution in which the CL-20 is dissolved and eventually crystallized is environmentally acceptable since it is free of chlorinated compounds and other compounds regulated as Hazardous Air Pollutants ("HAPs") under the Clean Air Act. Both the solvent and nonsolvent may be recycled for further processing without further treatment or purification.

The ε-polymorph CL-20 crystals may be combined with an appropriate amount of binder, plasticizer, fuel, inorganic oxidizers, curative, and/or other ingredients known in the art to make propellant, explosive, or pyrotechnic formulations. The preparation of propellants, explosives, and pyrotechnics, including the selection of appropriate ingredients and processing steps, is known in the art and, as such, is not described in detail herein. These ε-polymorph CL-20 crystals may be more easily processed into propellant, explosive, or pyrotechnic formulations than ε-polymorph CL-20 crystals crystallized by earlier or previous techniques.

The following examples serve to explain embodiments of the present invention in more detail. These examples are not to be construed as being exhaustive or exclusive as to the scope of this invention.

EXAMPLES

Example 1

2.0 Gram Crystallization of ε-Polymorph of CL-20 at 94° C.

2.0 grams of CL-20, 6.0 grams of ethyl acetate, 6.0 grams of benzyl formate, and 4.0 grams of STANPLAS® 100 were added to a single-neck, 250 ml round-bottom flask to form the crystallization solution. Once the CL-20 was dissolved, the crystallization solution was placed on a rotary evaporator and heated to a water temperature of 94° C. while a swirling motion was imparted to the crystallization solution. When the components of the crystallization solution had dissolved and the crystallization solution was homogenous, a vacuum was applied over the crystallization solution for approximately five minutes until about half of the ethyl acetate was removed. The vacuum was released while seed crystals of the ε-polymorph of CL-20 were added to the crystallization solution. The vacuum was reestablished and the temperature of the water bath was maintained at 94° C. until the ethyl acetate was completely removed. The crystals grew as the ethyl acetate was removed. The crystals remained in a slurry of benzyl formate and STANPLAS® 100. The slurry was cooled and the crystals were filtered and washed. 1.5 grams of the crystals were obtained, giving a yield of approximately 85%. Fourier transform infrared ("FTIR") analysis of the crystals showed that the ε-polymorph was obtained.

Example 2

200 Gram Crystallization of ε-Polymorph of CL-20 at 71° C.

400 grams STANPLAS® 100 and 600 grams benzyl formate were weighed into a 2-liter CL-20 reactor. The temperature of the water jacket was maintained at 71° C. The level of the liquids was marked. 200 grams of CL-20 was dissolved into 600 grams ethyl acetate and added to the CL-20 reactor. A vacuum of 10.5 cm Hg was applied over the crystallization solution. Approximately 27 minutes after the vacuum was applied, when approximately 40% of the ethyl acetate was removed, seed crystals of the ε-polymorph were added. The vacuum was reapplied and the temperature of the crystallization solution was maintained at 73° C. to 74° C. to remove the remainder of the ethyl acetate. Approximately 4 hours after the vacuum was initially applied, the crystals were filtered and washed with 2-propanol. An 85% yield of the crystals was obtained. FTIR analysis of the crystals showed the ε-polymorph was obtained.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of crystallizing an epsilon-polymorph of 2,4,6,8,10,12-hexanitro-2,4,6,8,10,12-hexaazatetracyclo [$5.5.0.0^{5,9}0^{3,11}$]-dodecane (CL-20), comprising:
    combining CL-20, at least one organic solvent, and at least one nonsolvent to form a crystallization solution;
    saturating the crystallization solution;
    heating the crystallization solution to a temperature of from about 71° C. to about 94° C.;
    removing the at least one organic solvent from the crystallization solution while retaining a sufficient amount of the at least one nonsolvent to crystallize the CL-20 as the epsilon-polymorph; and
    separating the at least one nonsolvent from the epsilon-polymorph of CL-20.

2. The method of claim 1, wherein combining CL-20, at least one organic solvent, and at least one nonsolvent to form a crystallization solution comprises combining the CL-20 with at least one organic solvent and at least one nonsolvent that are miscible with each other.

3. The method of claim 1, wherein combining CL-20, at least one organic solvent, and at least one nonsolvent to form a crystallization solution comprises combining the CL-20 with an effective amount of the at least one organic solvent to dissolve the CL-20.

4. The method of claim 1, wherein combining CL-20, at least one organic solvent, and at least one nonsolvent to form a crystallization solution comprises combining the CL-20, the at least one organic solvent, and at least one nonsolvent having a boiling point at least 10° C. higher than a boiling point of the at least one organic solvent.

5. The method of claim 1, wherein combining CL-20, at least one organic solvent, and at least one nonsolvent to form a crystallization solution comprises combining the CL-20, the at least one organic solvent, and at least one nonsolvent having a boiling point at least 15° C. higher than a boiling point of the at least one organic solvent.

6. The method of claim 1, wherein combining CL-20, at least one organic solvent, and at least one nonsolvent to form a crystallization solution comprises combining the CL-20, the at least one organic solvent, and at least one nonsolvent having a boiling point at least 20° C. higher than a boiling point of the at least one organic solvent.

7. The method of claim 1, wherein combining CL-20, at least one organic solvent, and at least one nonsolvent to form a crystallization solution comprises combining the CL-20, ethyl acetate as the at least one organic solvent, and a formate or an acetate as the at least one nonsolvent.

8. The method of claim 1, wherein combining CL-20, at least one organic solvent, and at least one nonsolvent to form a crystallization solution comprises combining the CL-20, ethyl acetate as the at least one organic solvent, and benzyl formate as the at least one nonsolvent.

9. The method of claim 1, wherein combining CL-20, at least one organic solvent, and at least one nonsolvent to form a crystallization solution comprises combining the CL-20, ethyl acetate as the at least one organic solvent, and benzyl acetate as the at least one nonsolvent.

10. The method of claim 1, wherein combining CL-20, at least one organic solvent, and at least one nonsolvent to form a crystallization solution comprises combining the CL-20, the at least one organic solvent, and at least one nonsolvent comprising at least one ester selected from the group consisting of an aryl formate and an aryl acetate.

11. The method of claim 1, wherein saturating the crystallization solution comprises evaporating the at least one organic solvent until a saturated or a supersaturated crystallization solution is formed.

12. The method of claim 1, wherein saturating the crystallization solution comprises adding additional CL-20 to the crystallization solution until a saturated or a supersaturated crystallization solution is formed.

13. The method of claim 1, wherein removing the at least one organic solvent from the crystallization solution comprises evaporating the at least one organic solvent.

14. The method of claim 1, further comprising adding a co-nonsolvent to the crystallization solution.

15. The method of claim 14, wherein adding a co-nonsolvent to the crystallization solution comprises adding naphthenic oil or paraffinic oil to the crystallization solution.

16. The method of claim 14, wherein adding a co-nonsolvent to the crystallization solution comprises adding the co-nonsolvent to the crystallization solution in a weight ratio that ranges from about 20:80 of the co-nonsolvent to the at least one nonsolvent to about 60:40 of the co-nonsolvent to the at least one nonsolvent.

17. The method of claim 1, further comprising adding epsilon-polymorph CL-20 seed crystals to the crystallization solution.

18. The method of claim 17, further comprising growing the epsilon-polymorph of CL-20 from the crystallization solution onto the epsilon-polymorph CL-20 seed crystals.

19. A method of crystallizing an epsilon-polymorph of 2,4,6,8,10,12-hexanitro-2,4,6,8,10,12-hexaazatetracyclo [$5.5.0.0^{5,9}0^{3,11}$]-dodecane (CL-20)>comprising:

combining CL-20, at least one organic solvent, and at least one nonsolvent to form a crystallization solution;

saturating the crystallization solution;

heating the crystallization solution to a temperature of from about 71° C. to about 130° C.;

removing the at least one organic solvent from the crystallization solution while retaining a sufficient amount of the at least one nonsolvent to crystallize the CL-20 as the epsilon-polymorph; and separating the at least one nonsolvent from the epsilon-polymorph of CL-20.

* * * * *

UNITED STATES PATENT AND TRADEMARK OFFICE
CERTIFICATE OF CORRECTION

PATENT NO. : 7,288,648 B2  
APPLICATION NO. : 10/636373  
DATED : October 30, 2007  
INVENTOR(S) : R. Scott Hamilton et al.

It is certified that error appears in the above-identified patent and that said Letters Patent is hereby corrected as shown below:

In the specification:
- COLUMN 6, LINE 46, change "F-polymorph" to --ε-polymorph--
- COLUMN 7, LINE 9, change "F-polymorph" to --ε-polymorph--
- COLUMN 7, LINE 35, change "F-polymorph" to --ε-polymorph--

In the claims:
CLAIM 19, COLUMN 11, LINE 6, change "(CL-20)>comprising" to --(CL-20), comprising--

Signed and Sealed this

Twenty-seventh Day of January, 2009

JOHN DOLL  
*Acting Director of the United States Patent and Trademark Office*